United States Patent [19]

Goel et al.

[11] Patent Number: 4,477,382

[45] Date of Patent: Oct. 16, 1984

[54] PREPARATION OF CARBOXYLIC ACID ANHYDRIDES

[75] Inventors: Anil B. Goel, Worthington; Harvey J. Richards, Columbus, both of Ohio

[73] Assignee: Ashland Oil, Inc., Ashland, Ky.

[21] Appl. No.: 451,826

[22] Filed: Dec. 21, 1982

[51] Int. Cl.³ ............................................. C07C 51/56
[52] U.S. Cl. ............................... 260/398; 260/545 R; 260/546
[58] Field of Search ................... 260/398, 545 R, 546, 260/545; 502/170, 201, 325; 252/420, 438, 472

[56] References Cited

U.S. PATENT DOCUMENTS 2,259,895  10/1941  Koenig ................................. 260/546
2,730,530  1/1956  Ohlson et al. ........................ 260/398
3,709,934  1/1973  Gruber et al. ................. 260/398 X

FOREIGN PATENT DOCUMENTS 616263  5/1978  U.S.S.R. .

Primary Examiner—Thomas A. Waltz
Attorney, Agent, or Firm—John F. Jones

[57] ABSTRACT

The conversion of a carboxylic acid having the formula RCOOH wherein R is a hydrocarbon group having from 1 to 20 carbon atoms to its corresponding anhydride by contacting said carboxylic acid with a salt of at least one metal selected from the group consisting of palladium, cobalt, manganese, chromium, nickel, copper, rhodium, iron and thorium at a temperature in the range of from about 120° to 300° C. is described.

14 Claims, No Drawings

PREPARATION OF CARBOXYLIC ACID ANHYDRIDES

This invention relates to a catalytic process for the formation of anhydrides from the corresponding carboxylic acids and more particularly pertains to the process for the dehydration of carboxylic acids to their corresponding carboxylic acid anhydrides by heating the carboxylic acid in the presence of a catalyst selected from the group consisting of salts of cobalt, manganese, palladium, chromium, nickel, iron, thorium, rhodium, copper, and mixtures thereof.

Carboxylic acid anhydrides have been prepared by several known procedures including the thermal dehydration of the carboxylic acid, the reaction of the carboxylic acid chloride with the carboxylic acid or salt thereof, the dehydration of the carboxylic acid with isocyanates and carbodiimides, the carbonylation of ethers and other methods as shown in R. Grimm, *Fatty Acids*, The American Oil Chemists Society, ed. by E. H. Pryde, P. 218, 1979.

The acid anhydrides of higher carboxylic acids have generally been prepared by reaction of the higher carboxylic acids with acetic anhydride.

We have discovered that carboxylic acid anhydrides can be dehydrated to form their anhydrides in the presence of certain metal salts.

The thermal dehydration of carboxylic acids to form their anhydrides has generally been carried out at temperatures greater than 300° C.

Our process can be conveniently carried out at a temperature in the range of from about 120° to 300° C. More preferably the temperature range of from about 140° to 220° C. is used in our process.

Carboxylic acids which can be dehydrated to the corresponding anhydride by our process are those corresponding to the formula RCOOH wherein R is a hydrocarbon group having from 1 to 20 carbon atoms including acetic acid, propionic acid, the butyric acids, the pentanoic acids, the hexanoic acids, the heptanoic acids, cyclohexane carboxylic acid, octanoic acid, decanoic acid, lauric acid, myristic acid and the like.

Metal salts which are useful catalysts in our process include palladium salts, cobalt salts, manganese salts, chromium salts, nickel salts, copper salts, rhodium salts, iron salts, thorium salts, and the like. Carboxylate salts of these metals are convenient catalysts in our process and preferred are the acetates such as palladium acetate, cobalt acetate, manganese acetate, chromium acetate, nickel acetate, copper acetate, rhodium acetate, iron acetate, thorium acetate and the like. Additional metal salts such as the alkali metal and/or alkaline earth metal acetates can be included along with one or more of the preferred acetates given just above.

The process of our invention can be carried out in a stirred reactor at a temperature in the range of from about 140° to 220° C. The water produced in our dehydration reaction can be removed in the form of an azeotrope with a hydrocarbon solvent such as heptane, benzene, toluene, etc. It is also usually preferred that our process be carried out in an inert atmosphere. When oxygen is present in any appreciable amount, some oxidation may take place which might lead to the formation of products other than the desired carboxylic acid anhydride.

The process of our invention will be further illustrated in the following specific examples.

EXAMPLE 1

A glass reactor of 500 ml. capacity and equipped with a mechanical stirrer, temperature control means and a Dean-Stark type condenser was employed. To the reactor were charged 43.5 g. (300 millimols) of octanoic acid and 0.74 g. (3 m mols) of $Co(OAc)_2.4H_2O$. About 7 ml. of heptane was also added to the reactor and the Dean-Stark tube was filled with heptane. The reaction mixture was stirred vigorously and heated to 200° C. and nitrogen was bubbled through the reaction mixture at the rate of 50 cc/minute. The reaction was allowed to proceed for 3 hours under these conditions during which about 1 ml of $H_2O$ was collected in the Dean-Stark tube. Infrared analysis of the reaction mixture at the end of the 3 hour reaction period showed bands characteristic of the anhydride at 1825 and 1760 $cm^{-1}$. GLC analysis of the reaction mixture showed that about 12% of the octanoic acid was converted to its anhydride to give 18 m mols of octanoic acid anhydride.

EXAMPLE 2

The procedure of Example 1 was repeated except that the reaction mixture was composed of 489 g (330 m mols) of octanoic acid, 1.35 g. (6 m mols) of $Pd(OAc)_2$ and 1.48 g. of $Cr(OAc)_3$. The reaction temperature was 160° C., oxygen was bubbled through the reaction mixture at the rate of 50 cc/min. and after 5 hours reaction time about 3 ml of water was collected in the Dean-Stark tube. Analysis showed that about 30% of the octanoic acid was converted to its anhydride (about 50 m mols).

EXAMPLE 3

The procedure of Example 1 was repeated except that 0.71 g (3 m mols) of $Mn(OAc)_2.4H_2O$ was charged instead of the cobalt acetate. The reaction was carried out at 205±5° C. for 3 hours under an atmosphere of nitrogen and 2 ml of water was collected in the Dean-Stark tube. GLC analysis of the mixture after reaction showed that 7 m mols of octanoic anhydride had been formed.

EXAMPLE 4

The procedure of Example 1 was repeated except that 1.66 g. of $Th(NO_3)_4.4H_2O$ (3 m mols) was used instead of the cobalt salt. The reaction was carried out for about 3 hours. GLC analysis of the product showed the formation of 1.2 m mols of octanoic acid anhydride.

EXAMPLE 5

The procedure of Example 1 was used except that 300 m mols of lauric acid were used instead of the octanoic acid. After 3 hours reaction time about 16 m mols of lauric acid anhydride had formed.

EXAMPLE 6

The procedure of Example 1 was repeated except that the reaction mixture was composed of 300 m mols of lauric acid and 0.51 g (2 m mols) of $Rh_2O_3$. The reaction temperature was 185±5° C. and after 4 hours reaction time 14 m mols of lauric acid anhydride were found to be present in the reaction mixture.

EXAMPLE 7

The procedure of Example 1 was repeated except that 44.5 g (308 m mols) of octanoic acid and 0.69 g (3 m mols) of $Cr(OAc)_3.H_2O$ were used. Octanoic acid was converted to octanoic acid anhydride in this manner.

EXAMPLE 8

The procedure of Example 1 was repeated using 0.6 g (3 m mols) of Cu(OAc)$_2$ in place of the cobalt salt. In about 3 hours reaction time 6 m mols of octanoic acid anhydride was formed.

EXAMPLE 9

The procedure of Example 1 was repeated except that 43 g (298 m mols) of octanoic acid, and 3 m mols each of Pd(OAc)$_2$, Sb(OAc)$_3$ and Cr(OAc)$_3$.H$_2$O were used. After a 3 hour reaction period 1.7 m mols of octanoic acid anhydride had formed.

EXAMPLE 10

When 0.52 g (3 m mols) of Fe(OAc)$_3$ was used in place of the cobalt salt in the procedure of Example 1 some octanoic acid anhydride was produced.

We claim:

1. The process for converting a carboxylic acid having the formula RCOOH wherein R is a hydrocarbon group having from 1 to 20 carbon atoms into its anhydride consisting essentially of contacting the carboxylic acid with a catalyst composed of the salt of at least one metal selected from the group consisting of palladium, cobalt, manganese, chromium, nickel, copper, rhodium, iron, and thorium at a temperature in the range of from 120° to 300° C.

2. The process of claim 1 wherein the salt is a carboxylate salt.

3. The process of claim 2 wherein the carboxylic acid is octanoic acid.

4. The process of claim 2 wherein the carboxylic acid is lauric acid.

5. The process of claim 3 wherein the salt is Co(OAc)$_2$.4H$_2$O.

6. The process of claim 3 wherein the salt is a mixture of Pd(OAc)$_3$ and Cr(OAc)$_3$.

7. The process of claim 3 wherein the salt is Mn(OAc)$_2$.4H$_2$O.

8. The process of claim 3 wherein the salt is Cr(OAc)$_3$.H$_2$O.

9. The process of claim 3 wherein the salt is Cu(OAc)$_2$.

10. The process of claim 3 wherein the salt is Fe(OAc)$_3$.

11. The process of claim 4 wherein the salt is Co(OAc)$_2$.4H$_2$O.

12. The process of claim 1 wherein the salt is Th(NO$_3$)$_4$.4H$_2$O.

13. The process for converting octanoic acid into its anhydride consisting essentially of contacting the acid with a catalyst composed of Pd(OAc)$_2$, Sb(OAc)$_3$ and Cr(OAc)$_3$.H$_2$O at a temperature in the range of from 120° to 300° C.

14. The process for converting lauric acid into its anhydride consisting essentially of contacting the acid with a catalyst composed of Rh$_2$O$_3$ at a temperature in the range of from 120° to 300° C.

* * * * *